Figure 1:
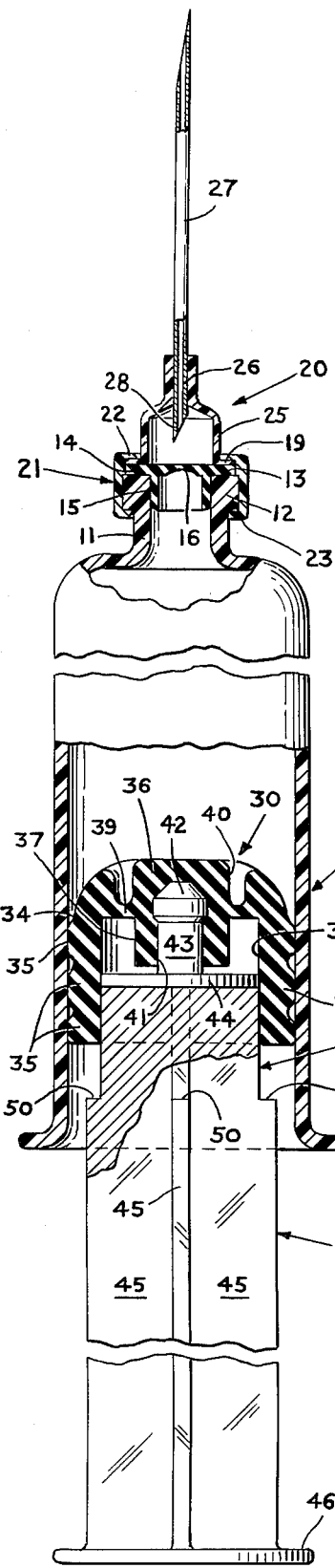

United States Patent [19]
Hansson et al.

[11] 3,939,833
[45] Feb. 24, 1976

[54] PISTON CONSTRUCTION FOR SYRINGES

[75] Inventors: Bengt Eve Hansson, Holden, Mass.; Edward A. Tischlinger, Niantic, Conn.

[73] Assignee: Astra Pharmaceutical Products Inc., Worcester, Mass.

[22] Filed: Jan. 15, 1975

[21] Appl. No.: 541,202

[52] U.S. Cl. ............................................ 128/218 P
[51] Int. Cl.[2] .......................................... A61M 5/00
[58] Field of Search ............ 128/218 D, 218 P, 219, 128/272.

[56]  References Cited
UNITED STATES PATENTS

| | | | |
|---|---|---|---|
| 1,738,146 | 12/1929 | Kulik | 128/218 D |
| 2,248,469 | 7/1941 | Smith | 128/218 D |
| 2,475,061 | 7/1949 | Smith | 128/218 D |
| 2,526,365 | 10/1950 | Jorgenson | 128/218 D |
| 2,895,773 | 7/1959 | McConnaughey | 128/219 X |
| 3,045,674 | 7/1962 | Goldberg | 128/218 P |
| 3,295,525 | 1/1967 | Evers et al. | 128/218 P |
| 3,340,872 | 9/1967 | Cox | 128/218 D |
| 3,543,755 | 12/1970 | Kessel | 128/218 P |
| 3,618,603 | 11/1971 | Levenson | 128/218 P |
| 3,710,794 | 1/1973 | Shields | 128/218 D |

Primary Examiner—John D. Yasko
Attorney, Agent, or Firm—John J. Hart

[57] ABSTRACT

A cartridge for a prefilled hypodermic syringe of the type sealed at its forward end with a destructible diaphragm is provided with a piston-piston rod assembly in which the piston of resilient material is molded in the form of a hollow cylinder and has an auxiliary short, cup-shaped member of reduced diameter coaxially enclosed within its forward end, and sealed in yieldable engagement with the inner walls of said hollow cylinder by a transverse, annularly-shaped elastic membrane. The piston rod has a forward portion of lateral cross-section smaller than the inner cross-sectional area of the piston and slidably receivable in the latter, and a following portion having a lateral cross-section dimension greater than the inner cross-sectional area of the piston, the junction of the two rod portions forming a forwardly directed shoulder. When the piston rod is actuated, the forward reduced portion slides forwardly in the piston until it engages the auxiliary member and causes such member to distend forwardly, while the main body of the piston remains stationary. Continued actuation of the piston rod then brings the shoulder formed by the following rod portion into engagement with the main body of the piston to cause the piston to move as a whole within the syringe cartridge.

3 Claims, 3 Drawing Figures

PISTON CONSTRUCTION FOR SYRINGES

THE INVENTION

This invention relates to piston constructions and more particularly to a piston which is especially useful in connection with prefilled hypodermic syringes of the disposable type which are provided at their forward ends with a closure composed of a destructible diaphragm.

A disposable, prefilled hypodermic syringe of the indicated type usually comprises a rigid, tubular cartridge of glass or other suitable material, provided at one end with a piston and piston rod assembly, and provided at the other end, which may be constricted to form a neck of reduced diameter, with a penetrable closure for sealing the contents of the cartridge. The cartridge is also provided at such other end with a closure-piercing means such as the pointed end of a hypodermic needle and which is mounted in spaced relationship with said penetrable closure to prevent accidental puncture and contamination or release of the contents of the cartridge. The syringe may be constructed to have the penetrable closure pierced by movement of the needle or other closure-piercing means relative to the cartridge, or to have a closure which may be ruptured by forcing, stretching or ballooning it into contact with the piercing means provided in the structure.

In the illustrated embodiment of the invention, the improvement thereof is utilized with a syringe having a flexible, membrane-like closure which is caused to stretch or balloon by reason of fluid pressure created in the column of fluid contents of the cartridge when the piston-piston rod assembly is actuated.

A relatively small force or pressure need be exerted on the piston of a cartridge of small diameter, such as a cartridge having a volume of up to 5 ml., for example, to stretch or balloon the membrane closure thereof to the required extent for destruction. However, cartridges of larger bore for volumes up to, for example, 50 ml., require substantially higher pressures proportional to the surface area of the piston to effect proper stretching or ballooning of their membrane closures. For example, the average pressure required to rupture the diaphragm on a 5 ml. cartridge having a piston of 1.2 cm. diameter is 8 pounds. A cartridge having a capacity of 50 ml., and provided with a plunger of 3 cm. diameter, requires approximately 50 pounds pressure to rupture the diaphragm.

The principal purpose of the present invention is to provide an improved piston contruction which will enable the membrane closures in cartridges having a capacity of from 5 to 50 and higher ml. to be ruptured by applying to the piston rods thereof a relatively small force.

In accordance with the aforesaid object, the present invention provides a novel piston construction for syringes having large volume cartridges, that causes the force exerted thereon by the operator to be transmitted to the stretchable membrane closure of the syringe through an auxiliary piston member of small cross-sectional area, thereby reducing the pressure or driving force which is required to be applied to the piston to effect rupture of the closure. While the invention will be hereinafter described in connection with a disposable hypodermic syringe of a particular construction, it will be readily apparent that this same piston structure could be employed in connection with other types of closures or sealing means for cartridges in which the release of the contents of the cartridges is effected by movement or action on the sealing means thereof through pressure applied by an operator to the pistons thereof.

In the type of syringes with which this invention is particularly concerned, the piston is normally molded of resilient material having the characteristics of soft rubber, in the form of a hollow cylinder or cup which is closed at one end and has annular grooves in axially spaced relation to increase the efficiency of the seal with the inner wall of the cartridge. The inner-facing or closed end of such a piston may be slightly shaped, but is generally smooth surfaced. The following or outer end may be hollow and threaded, or otherwise formed, to accept and hold a piston rod through which the driving force is transmitted by the operator to the piston.

The body of a piston made in accordance with the present invention is molded in the form of a cylinder having an annular wall of sufficient thickness to engage the walls of the cartridge, and has an auxiliary cup-shaped member of reduced diameter coaxial with the cylinder and held in yieldable engagement with it by a transverse, annularly-shaped, elastic membrane. The inner portion of the auxiliary cup-shaped member may be formed to engage a mating protuberance on the piston rod.

The forward section of the piston rod is smaller in lateral cross-section than the remainder of the rod. The lateral cross-sectional and longitudinal dimensions of such smaller piston rod section are such as to enable such piston rod section to slidably travel within the opening in the piston and into engagement with the inner end of the auxiliary member to distend the latter without movement of the annular wall of the piston, the longitudinal dimension or length of such rod section being sufficient to enable the auxiliary member to be advanced a given distance.

The remaining length of the piston rod has a cross-sectional dimension greater than that of the opening in the piston and less than the outer diameter of the annular wall or main body of the piston so that when the auxiliary member of the piston has been distended to the maximum distance desired, continued application of pressure to the piston rod will cause a forwardly directed shoulder formed by such piston rod section and the remaining length of the rod to engage such main body of the piston and move the piston as a whole within the cartridge to discharge the contents of the cartridge.

It is to be noted that in the use of the improved piston construction of this invention, when a relatively small force is applied to the piston rod, the auxiliary piston member is distended forwardly while the main body of the piston remains stationary within the cartridge. The force that is thus transmitted through the fluid column by such distention of the auxiliary member is sufficient to cause the rupture of the sealing closure. With the resistance of the sealing closure removed and the body of the piston rod engaged directly with the main body of the piston only nominal force is required to be exerted on the piston to effect the discharge of the contents of the cartridge.

Figure 2:
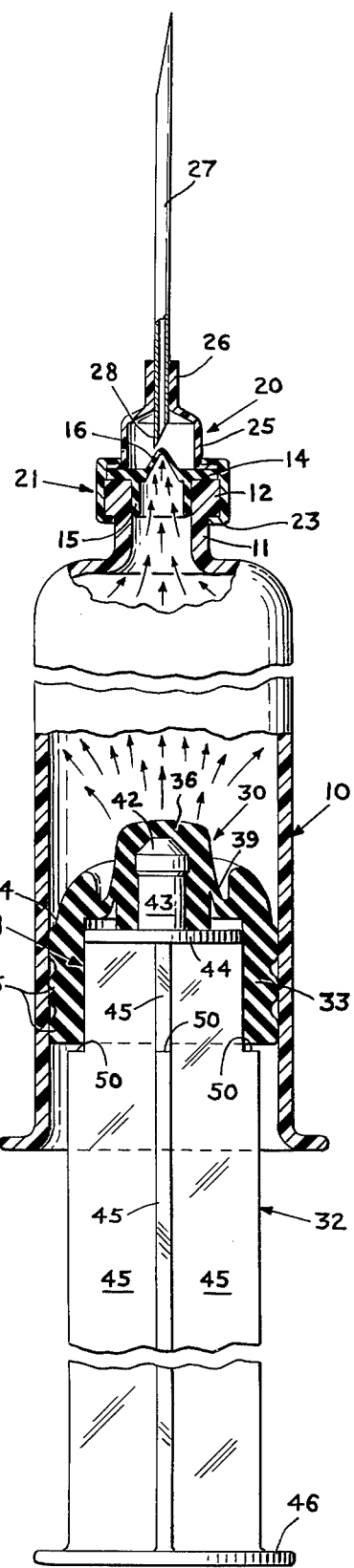
Figure 3:
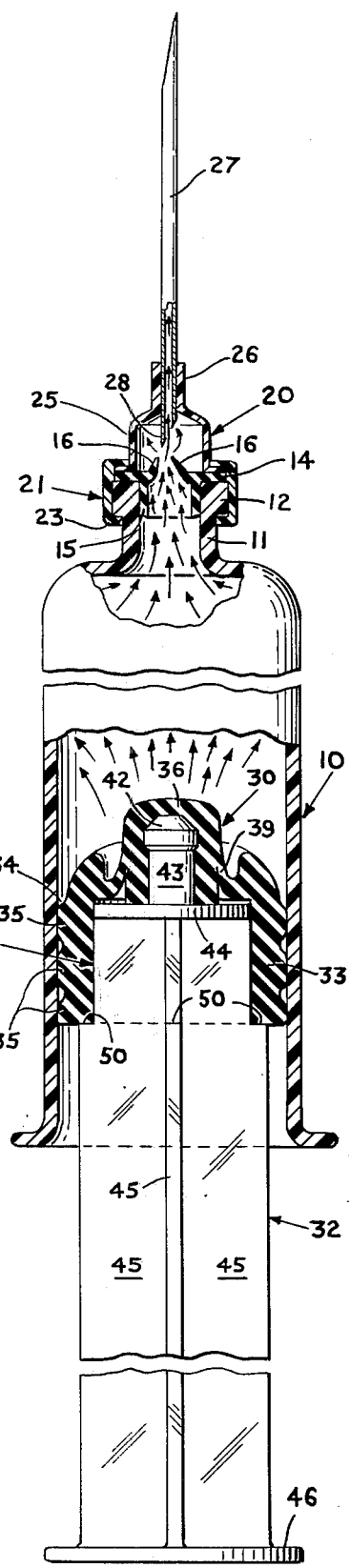

Other advantages of the piston construction of this invention, as well as the features of novelty thereof, will appear from a consideration of the following description when read in connection with the accompanying drawings; in which FIG. 1 is a side view, partly in section, of a disposable hypodermic syringe embodying the invention and showing the syringe in the condition in which the contents are still sealed in the cartridge thereof;

FIG. 2 is a similar view showing the syringe piston rod advanced to the extent that the auxiliary piston member has been distended sufficiently to bring the sealing diaphragm at the reduced end of the syringe into a condition for rupture by a needle point provided for such purpose; and FIG. 3 is a similar view showing the piston advancing as a whole to discharge the contents of the cartridge into a needle, cannula, or other delivery means.

In the drawings, the reference numeral 10 designates generally the cartridge of a disposable hypodermic syringe. At its discharge end, the cartridge is provided with a neck 11 and an external flange 12 having an outer planar surface 13. Seated on the surface 13 is the flange portion 14 of a closure or stopper having a tubular plug portion 15 which snugly engages the interior wall of the neck 11. The stopper is made of a resilient, compressible material such as rubber and its tubular portion 15 is sealed off by a very thin wall or membrane 16 which is integral with the portions 14 and 15 of the stopper. The membrane 16 is capable of stretching and thinning out under the influence of pressure applied to the under surface in the manner of an inflatable thin walled rubber balloon as is indicated in FIG. 2 of the drawings.

Seated on the outer surface of the closure flange 14 is the outwardly flanged lower end 19 of the needle mounting 20. The flange 19 is firmly clamped to the outer surface of the closure flange 14 by a suitable clamping ring 21 having an outer inturned flange 22 engaging the outer surface of the mounting flange 19. The outer end 23 of the clamping ring is crimped around the inner end of the cartridge flange 12. The clamping ring 21 thus holds the needle mounting 20, the cartridge stopper and the cartridge together.

The inner end 25 of the needle mounting 20 which is provided with the flange 19, is cylindrically-shaped. At a place spaced from the membrane 16 of the stopper, the mounting 20 tapers inwardly and terminates in a cylindrically-shaped needle holder 26. Extending through the holder 26 and having an intermediate portion thereof permanently gripped by such holder in any suitable fashion is a hypodermic needle 27. The outer projecting portion of the needle 27 is of such length as may be found desirable for the particular use of the syringe and is pointed at its outer terminal end. The inner portion 28 of the needle within the mounting 20 extends through the space defined by the cylindrical and tapering portions of the mounting toward the membrane 16 and has a pointed end which terminates a short distance away from the membrane 16. The space between the membrane 16 and the pointed end of the inner portion 28 of the needle is such that when such membrane bulges into the space provided within the mounting 20 under fluid pressures exerted thereon from within the cartridge 10, as is shown in FIG. 2, the membrane will come into contact with the point on the inner portion 28 of the needle and be ruptured.

The medicament in the cartridge 10 is sealed between the diaphragm 16 and a piston 30 provided on the head 31 of a piston rod 32. The piston 30 is generally cup-shaped and made of a suitable resilient material, such as rubber. The body 33 of the piston is tubularly-shaped and relatively thick walled so that it takes relatively large pressures to compress it longitudinally. The exterior cylindrical surface 44 of the piston 30 has a diameter slightly less than the interior diameter of the tubular barrel of the cartridge 10. The surface is provided with integral spaced annular ridges or protuberances 35 of a diameter greater than the interior diameter of the tubular barrel of the cartridge 10 so that they press with sufficient force against the interior barrel wall to provide a seal against the escape of liquid past the piston.

Surrounded by the forward end of the piston body 33 is a cup-shaped auxiliary piston member 36 formed integrally with such body but having an exterior cylindrical surface 37 spaced from the interior cylindrical surface 38 of the cup body 33. The auxiliary piston member 36 is connected to the cup body 33 by an integral transverse annular membrane 39 capable of stretching and thinning out under relatively little stress to enable the auxiliary member 36 to move forwardly relative to the cup body 33 and of restoring such parts to normal arrangement upon removal of such stress. In the normal arrangement of the main body of the piston 33 and the auxiliary piston member 36, the forward rounded end of such body and the forward closed end of the auxiliary piston member are substantially flush and give the forward end of the piston 30 a crowned configuration having provided therein an annular recess 40, the inner end of which is closed by the transverse annular membrane 39. The auxiliary piston member 36 is also cup-shaped and is provided with a cylindrically-shaped recess 41 which is open at the following end of said member. The inner end of the recess 41 is enlarged and configured to receive a formed knob 42 located on the outer end of a connecting rod 43 of reduced cross-sectional area. The connecting rod 43 extends through the opening 41 and is secured at its other end to the central portion of a disc 44 forming the forward terminal end of the head 31 of the piston rod 32. The connecting rod 43 and knob 42 are coaxial with and form a forwardly projecting extension of the piston rod head 31. As the form of the rod 43 and knob 42 conform to the configuration of the recess 41 they form a mating projection which securely fastens the auxiliary piston member 36 in locked relation to the piston rod 32.

At the following end of the piston rod 32 there is provided a disc-shaped, fingers engageable member 46 for actuating the piston rod. The body of the piston rod 32 between member 46 and the head 31 thereof, and such head 31, are constituted of an integral piece of plastic material molded to provide four radial, 90° disposed longitudinally extending flanges 45 forming a "beam" type of piston rod. The radial dimension of the portions of the flanges 45 forming the body or main portion of the piston rod 32 is greater than the radius of the internal cylindrical surface 38 of the piston body 33, but less than the internal radius of the barrel of the cartridge 10. The radial dimension of the portions of the flanges 45 forming the piston rod head 31 is less than that of the flange portions forming the main portion of the piston rod 32, similar to that of the disc 44, and approximating the radius of the internal surface 38 of the piston so as to enable such piston rod head 31 to slidably move within such surface 38. Due to the difference between the radial dimensions of the portions of the flanges 45 in the piston rod head 31 and the portions of such flanges constituting the main portion of the piston rod there is formed at the junctures of such flange portions outwardly projecting shoulders 50. The length of the piston rod head 31 is such as to permit the auxiliary piston member 36 to travel the distance required to effect the rupture of the closure seal 16 before the shoulders 50 come into engagement with the open end of the cup body 33 to advance the piston 30 as a whole to discharge the contents of the syringe cartridge 10 through the needle 27.

It will be understood from the foregoing that in the use of a syringe provided with a piston assembly embodying the invention, a relatively small force applied to the piston rod 32 will initially advance the forward portion 31 of the piston rod within the piston body 33 which because of its frictional contact with the internal wall of the syringe barrel 10 will remain stationary until the shoulders 50 on piston rod 32 come into contact with the outer end of such piston body. During such advancement the forward portion 31 of the piston rod will force the auxiliary piston member 36 forwardly as shown by comparison of FIGS. 1 and 2. As is also shown in such figure, the advancing auxiliary piston member 36 will exert a force through the liquid column as is indicated in FIG. 2 by the arrows 51. This force exerted through the liquid contents of the syringe will cause the diaphragm 16 to balloon outwardly toward the inner point of the needle 27. By the time the piston rod has advanced to the extent that the shoulders 50 thereof come into engagement with the open end of the piston 33, the force exerted in the liquid contents of the syringe by the advancing auxiliary piston member 36 will have caused the diaphragm 16 to balloon to the extent that it has come into engagement with and has been ruptured by the needle 27. With the rupture of the diaphragm or membrane 16 which permits a free flow of the liquid contents toward the inner end of the needle 27, a nominal force only need be exerted on the piston rod 32 to advance the piston 30 as a whole for complete discharge of the contents of the cartridge through the needle 27. The nominal force required for this purpose is only a fraction of the amount of force that would otherwise be required if a solid piston cap of the same size were operated as a single element to effect the destruction of the membrane 16.

While there has been described hereinabove and illustrated in the drawings, a preferred embodiment of the invention, it will be apparent to those skilled in the art that various changes may be made thereto without departing from the spirit of the invention or the scope of the appended claims. For example, the mating projection composed of the connecting rod 43 and knob 42 may be dispensed with without a material difference in the effectiveness of the two step action of the piston 30. It is also apparent that the disc 44 is not necessary for a proper operation of the piston. With the absence of the disc the forward ends of the flanges 45 will provide an adequate engagement between the piston rod head 31 and the following end of the auxiliary piston member 36. Instead of being constructed as a beam type of piston rod, the piston rod 32 may be made in the cylindrical form so that there will be formed between the body of the piston rod and the head thereof an annularly-shaped shoulder 50.

What is claimed is:

1. In a prefilled, disposable hypodermic syringe, or cartridge intended therefor, of the type sealed at its foward end with a destructible diaphragm, a piston and piston rod construction comprising:

a. a unitary piston of molded resilient material and composed of a main piston body constituted of a hollow cylinder having an annular inner wall and an exterior formed to sealably engage the inner surface of a syringe barrel;

b. an auxiliary member or reduced diameter and substantially shorter than said hollow cylinder coaxially enclosed within the forward end of said main cylindrical piston body with the external surface of said auxiliary member spaced from said inner piston body wall, and c. a transverse, annularly-shaped elastic membrane connecting said auxiliary member in yieldable sealed engagement with the inner wall of said main cylindrical piston body;

d. a piston rod having a forward portion and a following portion fixedly connected together, and movable as a unit relative to the main piston body, said forward portion having a lateral cross-section dimension approximating the inner cross-sectional area of the main piston body and slidably engageable with the inner wall of said main piston body, said forward portion being of such length that when advanced within the chamber formed by the inner wall of said main piston body it comes into contact with the inner-facing end of the auxiliary member spaced from such inner wall and moves said member forwardly for a predetermined distance limited by the length of said forward position without causing movement of said main piston body, the outer-facing end of the auxiliary member having an area substantially less than the cross-sectional area of the syringe barrel and such that as said member moves through such predetermined distance while said main piston body remains stationary, it exerts a forwardly directed force through the liquid contacts in the syringe barrel sufficient to rupture the distructible diaphragm; and e. a forwardly directed shoulder formed by said forward piston rod portion and the following portion of said piston rod, and having a lateral cross-section dimension greater than the inside diameter of said main piston body so that when the auxiliary member has been distended to the desired distance, continued application of pressure to the piston rod will cause such shoulder to engage the main piston body and to coact with said forward piston rod portion in engagement with the auxiliary member to move the piston as a whole with said auxiliary member distended within the syringe barrel.

2. A piston as defined in claim 1, in which said annular membrane is connected to said main piston body at a place spaced from the advanced end thereof and to an intermediate part of said auxiliary piston member, the outer-facing end of said auxiliary member being substantially flush with the advanced facing end of said main piston body and said membrane, main piston body and auxiliary piston member forming an annular recess in the advanced end of said piston, the inner end of said auxiliary piston member projecting into and terminating in the chamber formed by the inner wall of said main piston body and slidably receiving said forward piston rod portion.

3. A method for reducing piston pressures required to rupture or otherwise dispose the seal of a prefilled, disposable hypodermic syringe of large volume, sealed at its forward end by a destructable diaphragm, comprising utilization of:

a. a piston of resilient material having a main body molded in the form of a hollow cylinder with an annular wall in sealable relation with the inner wall of a syringe body and having an auxiliary member of reduced diameter and substantially shorter length coaxially enclosed within the forward end of said main cylindrical piston body, so that the inner end of such auxiliary member is spaced from such annular wall and terminates in the space defined thereby, the auxiliary member being sealed in yieldable engagement with the annular wall by a transverse, annularly-shaped, elastic membrane;

b. a piston rod coacting with said piston having a forward portion and a following portion fixedly connected thereto so that they are movable as a unit relative to the main portion body, the forward portion being slidably engageable with the inner side of the annular main piston body wall, and of such length that when advanced within said piston into contact with the inner-facing end of said auxiliary piston member, said member is distended forwardly for a desired distance while the main body portion remains stationary, the outer-facing end of the auxiliary piston having such area that as it is distended it exerts a forwardly directed force through the liquid contents of the syringe sufficient to balloon the diaphragm, and said forward portion forming with the following portion of said piston rod a forwardly directed shoulder of lateral cross-section dimension greater than the inside diameter of said main body so that when the auxiliary piston member has been distended to the desired distance, continued application of pressure to the piston rod will cause it to engage the main body of the piston and move it within the syringe body, whereby;

pressure exerted on the fluid column by the coaction of the forward portion of the piston rod with the annular main piston body wall and the auxiliary piston member without movement of the main piston body during the travel of such member during the desired distance ruptures or otherwise disposes the seal, and continued pressure on the piston rod engages the shoulder of the piston rod with the main body of the piston causing it and the auxiliary piston member to move as a whole within the syringe body for discharge of the contents of the syringe.

* * * * *